(12) United States Patent
Moake et al.

(10) Patent No.: US 6,604,581 B2
(45) Date of Patent: Aug. 12, 2003

(54) FLUID PROPERTY SENSORS AND ASSOCIATED METHODS OF CALIBRATING SENSORS IN A SUBTERRANEAN WELL

(75) Inventors: Gordon L. Moake, Houston, TX (US); Eugene Linyaev, Houston, TX (US); Robert A. Moore, Katy, TX (US); John P. Rogers, Houston, TX (US)

(73) Assignee: Halliburton Energy Services, Inc., Dallas, TX (US)

( * ) Notice: Subject to any disclaimer, the term of this patent is extended or adjusted under 35 U.S.C. 154(b) by 32 days.

(21) Appl. No.: 10/007,366

(22) Filed: Oct. 22, 2001

(65) Prior Publication Data

US 2002/0121371 A1 Sep. 5, 2002

(30) Foreign Application Priority Data

Oct. 23, 2000 (WO) ............................... PCT/US00/29254

(51) Int. Cl.⁷ .............................................. E21B 47/00
(52) U.S. Cl. ........................... 166/250.07; 166/250.15; 166/250.17; 166/369; 166/66
(58) Field of Search .................. 166/250.01, 250.07, 166/250.15, 250.17, 369, 66, 185, 64

(56) References Cited

U.S. PATENT DOCUMENTS

| | | | |
|---|---|---|---|
| 3,224,267 A | 12/1965 | Harlan et al. | |
| 5,101,907 A | * 4/1992 | Schultz et al. | |
| 5,204,529 A | * 4/1993 | Diatschenko | |
| 5,730,219 A | 3/1998 | Tubel et al. | |
| 5,829,520 A | * 11/1998 | Johnson | |
| 5,831,177 A | 11/1998 | Waid et al. | |
| 6,082,454 A | 7/2000 | Tubel | |
| 6,082,455 A | 7/2000 | Pringle et al. | |

FOREIGN PATENT DOCUMENTS

GB 2325949 A 12/1998

OTHER PUBLICATIONS

Partial Search Report For PCT Application No.: PCT/US00/29254.

* cited by examiner

Primary Examiner—Roger Schoeppel
(74) Attorney, Agent, or Firm—Marlin R. Smith (57) ABSTRACT

Fluid property sensors and associated methods of calibrating sensors in a well provide enhanced well monitoring and control. In one described embodiment, an external venturi flowmeter is utilized to determine a flow rate of fluid from a zone into a tubing string, independent of flow into the tubing string of fluid produced from any upstream zone. In another described embodiment, a gamma ray fluid density sensor utilizes a unique combination of gamma ray sources and detectors to determine a density of fluid flowing through a tubing string. In yet another embodiment, external tubing string sensors are used to determine properties of fluid from a zone into a tubing string, independent of flow into the tubing string of fluid produced from any upstream zone. In still another embodiment, sensor systems for multiple independently produced zones are calibrated.

18 Claims, 7 Drawing Sheets

FLUID PROPERTY SENSORS AND ASSOCIATED METHODS OF CALIBRATING SENSORS IN A SUBTERRANEAN WELL

CROSS-REFERENCE TO RELATED APPLICATION

This application claims the benefit under 35 USC §119 of the filing date of PCT Application No. PCT/US00/29254, filed Oct. 23, 2000, the disclosure of which is incorporated herein by this reference.

BACKGROUND

The present invention relates generally to fluid property measurement in a subterranean well and, in an embodiment described herein, more particularly provides fluid property sensors and methods of calibrating same.

It is very beneficial to be able to independently control production from each one of multiple zones of a well. For example, when water begins to be produced from a particular zone, it may be desired to cease production from that zone, while still producing from other zones of the well. As another example, when gas begins to be produced from a particular zone, it may be desired to decrease production from that zone, while still producing from other zones of the well. As a further example, rates of production from various zones may be independently regulated to maximize overall production from a reservoir.

However, in order to accurately determine the particular zones to regulate production from, and the manner in which production from those zones should be regulated, a well operator needs to be able to determine what fluids, and what quantities of those fluids, are being produced from each zone. Prior methods of making these determinations have relied on use of wireline conveyed tools. However, use of these tools usually requires that the well be shut in and that an intervention be made into the well.

It would be far more convenient and useful to be able to continuously monitor what fluids, and what quantities of those fluids, are being produced from each zone of a well. It is accordingly one of the objects of the present invention to provide fluid property sensors for relatively permanent installation in a well, and methods of using and calibrating those sensors.

SUMMARY

In carrying out the principles of the present invention, in accordance with embodiments thereof, fluid property sensors and associated methods are described herein. In the described embodiments, the sensors and methods are utilized to facilitate monitoring and control of production from multiple zones of a well. However, it is to be understood that the sensors and methods may also be used in other situations.

In one aspect of the present invention, sensors in fluid communication with an annulus external to a tubing string are used to measure properties of fluid flowing from a zone into the tubing string. By using such external sensors for each zone of a well, properties of the fluid produced from each zone may be determined prior to the fluid entering the tubing string. Thus, the properties measured by the external sensors are indicative of the fluid produced from a zone prior to it being commingled in the tubing string with fluid produced from other zones.

In another aspect of the present invention, an external venturi flowmeter is provided. The flowmeter is interconnected in a tubing string and positioned in a wellbore. Fluid flowing from a zone through an annulus between the wellbore and the tubing string is constrained to pass through a flow restriction due to a projection formed on a housing of the flowmeter. A differential pressure gauge measures a differential pressure between the fluid upstream of the flow restriction and the fluid flowing in the flow restriction. In this manner, a rate of flow of fluid produced from a zone may be determined before the fluid is commingled in the tubing string with fluid produced from other zones.

In yet another aspect of the present invention, a fluid density sensor is provided. The fluid density sensor uses a unique combination of gamma ray sources and detectors to enable its relatively permanent installation in a well. In the described embodiment, gamma ray sources exempt from certain regulations and Geiger-Muller gamma ray detectors are used. An additional detector is used to determine the contribution of background gamma ray sources to the measured rate of gamma rays received.

In a further aspect of the invention, the fluid density sensor is combined with other sensors in a sensor system, measurements from which may be used to determine a volumetric flow rate of each phase of fluids produced through a tubular string. The sensor system may be positioned in the string downstream of a flow control device regulating fluid flow into the string from a zone.

In a still further aspect of the invention, multiple ones of the sensor systems and flow control devices may be used in a well having multiple independently produced zones. A method of calibrating the sensor systems is provided, whereby measurements obtained from each of the sensor systems may be calibrated. The use of the calibrated multiple sensor systems enables determination of the volumetric flow rate of each phase of fluids produced from each of the zones.

These and other features, advantages, benefits and objects of the present invention will become apparent to one of ordinary skill in the art upon careful consideration of the detailed description of representative embodiments of the invention hereinbelow and the accompanying drawings.

DETAILED DESCRIPTION

Figure 1:
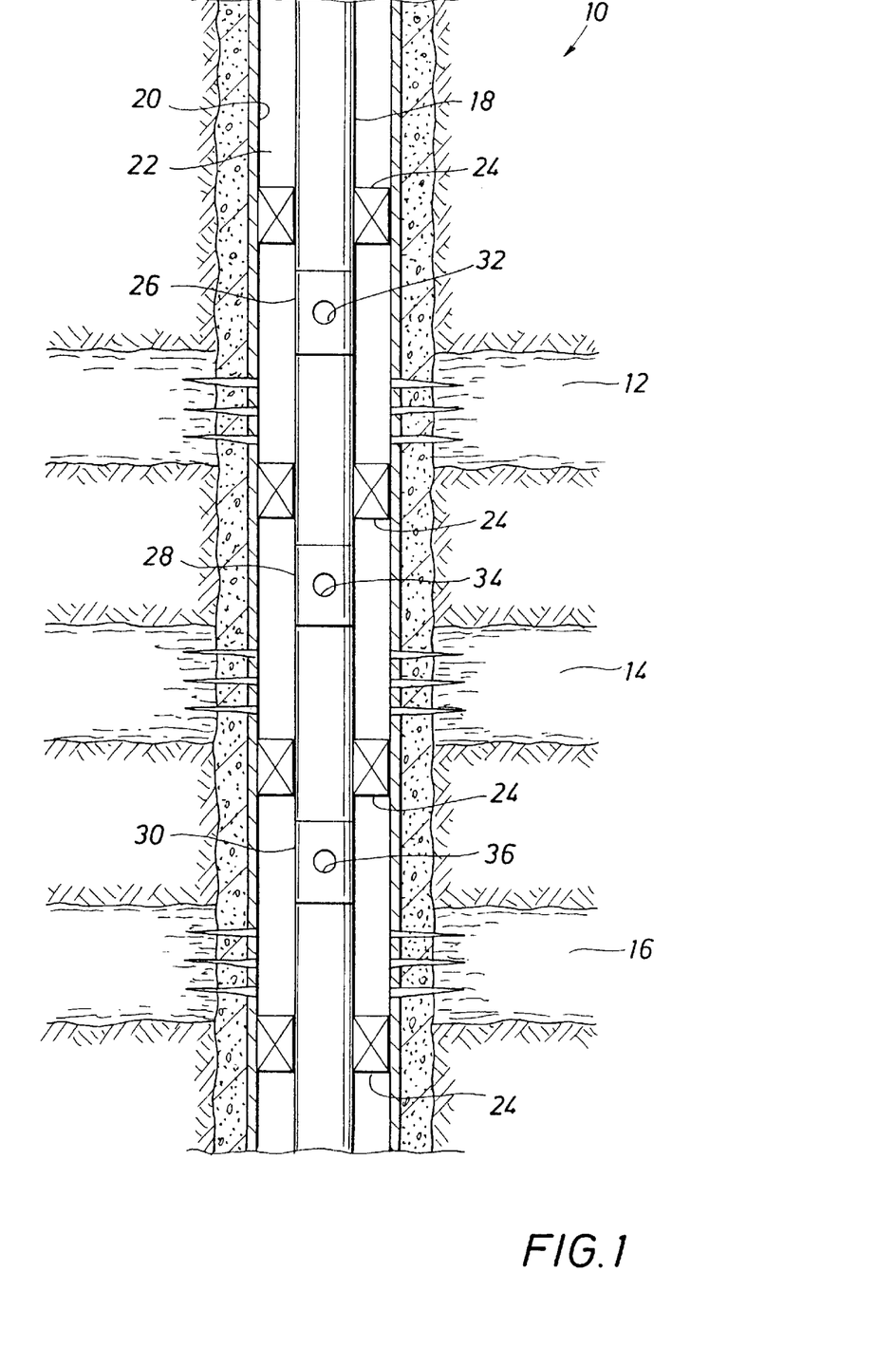
FIG. 1 is a schematic view of a first method of sensing fluid properties in a subterranean well, the method embodying principles of the present invention.

Representatively illustrated in FIG. 1 is a method 10 which embodies principles of the present invention. In the following description of the method 10 and other apparatus and methods described herein, directional terms, such as "above", "below", "upper", "lower", etc., are used only for convenience in referring to the accompanying drawings. Additionally, it is to be understood that the various embodiments of the present invention described herein may be utilized in various orientations, such as inclined, inverted, horizontal, vertical, etc., and in various configurations, without departing from the principles of the present invention.

In the method 10, it is desired to determine properties of fluid produced from multiple zones 12, 14, 16 into a tubing string 18. The tubing string 18 is positioned in a wellbore 20 intersecting the zones 12, 14, 16. An annulus 22 is formed radially between the wellbore 20 and the tubing string 18. Packers 24 isolate portions of the annulus 22 from each other. Flow control devices 26, 28, 30 permit selective control of fluid flow between each of the zones 12, 14, 16 and an interior flow passage (not visible in FIG. 1) of the tubing string 18.

It is very beneficial to be able to determine the properties of the fluid flowing from each of the zones 12, 14, 16 into the tubing string 18. For example, one of the zones 12, 14, 16 may begin producing water, in which case it would be beneficial to know which one of the zones is producing water, so that it may be determined which of the flow control devices 26, 28 or 30 should be closed. As another example, it may be beneficial for purposes of maximum recovery from a reservoir to accurately regulate the flow from each zone 12, 14, 16, depending at least in part on the types and relative quantities of fluids produced from the zones. In that case, the flow control devices 26, 28, 30 may be variable chokes which are operable to regulate a rate of fluid flow through respective ports 32, 34, 36 thereof, to thereby control the rate of fluid produced from each corresponding zone 12, 14, 16.

Note that, although the method 10 is depicted in FIG. 1 as being performed with three zones 12, 14, 16 intersected by a cased and cemented wellbore 20, it is to be clearly understood that any number of zones may be intersected by any type of wellbore, including lined or open hole wellbores, etc., in a method incorporating principles of the present invention. The principles of the present invention are not limited by the specific details of the method 10, which is described herein as merely an example of an embodiment of the invention.

Figure 2:
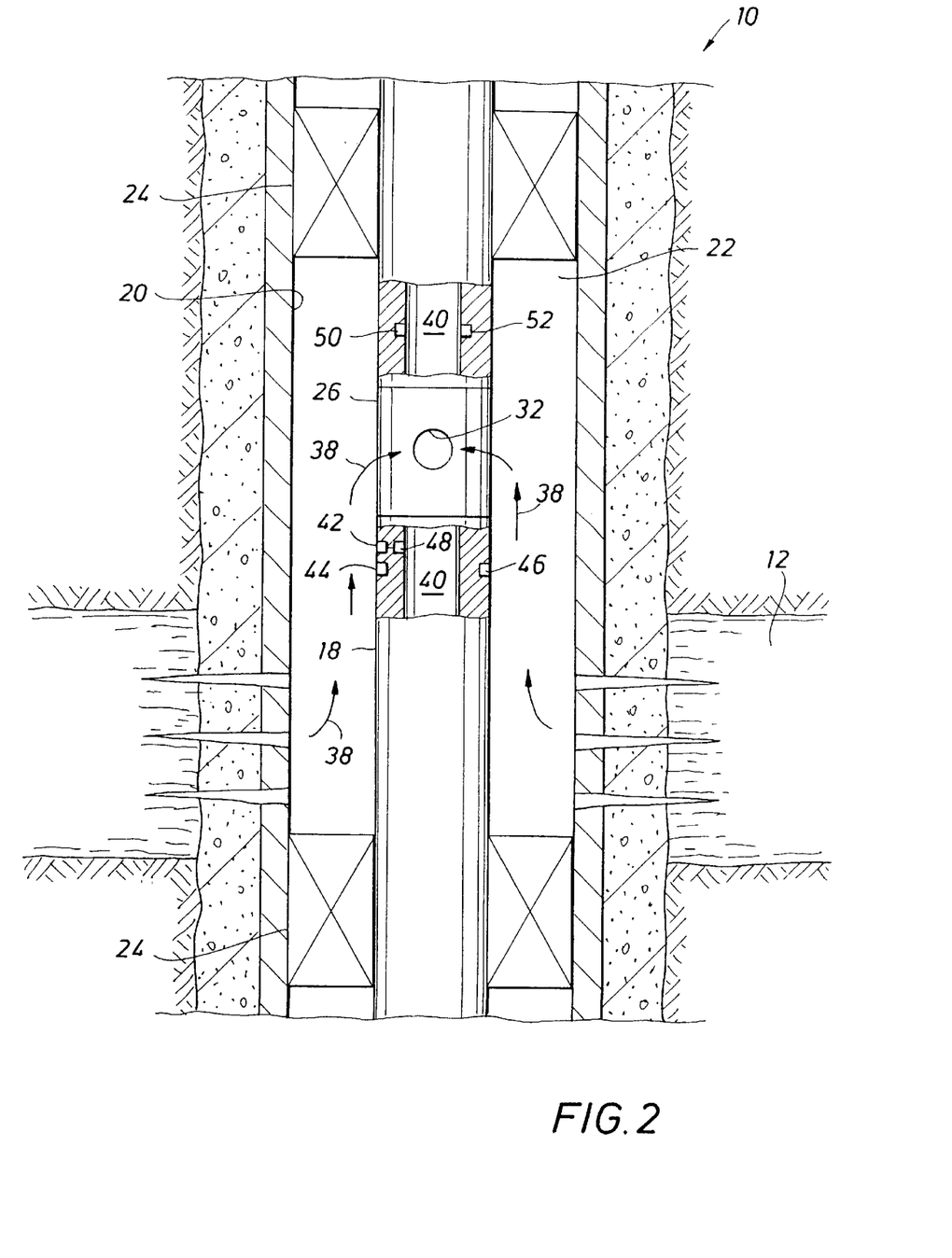
FIG. 2 is an enlarged scale schematic partially cross-sectional view of a first sensor system for an individual zone of a multizone completion, the first sensor system being usable in the first method of FIG. 1 and embodying principles of the present invention.

Referring additionally now to FIG. 2, an enlarged partially cross-sectional view of a portion of the well shown in FIG. 1 is representatively illustrated. Specifically, the flow control device 26 and the corresponding zone 12 are depicted in FIG. 2. In this view it may be clearly seen that the tubing string 18 is positioned in the wellbore 20 and configured so that fluid (represented by arrows 38) flows from the zone 12, flows externally across an exterior surface of the tubing string 18, into the port 32, and then into the internal flow passage 40 of the tubing string.

In the method 10, sensors 42, 44, 46 are in fluid communication with the fluid 38 as it flows externally across the tubing string 18 from the zone 12 to the port 32. In this manner, properties of the fluid 38 may be sensed before the fluid enters the tubing string 18 flow passage 40, where the fluid may be commingled with fluid from other zones.

The sensors 42, 44, 46 may be any of a fluid capacitance sensor, a fluid dielectric sensor, a fluid resistivity sensor, a fluid conductivity sensor, a nuclear fluid density sensor, an acoustic fluid density sensor, a fluid pressure sensor, a temperature sensor, a fluid compressibility sensor, a fluid pH sensor, or any other type of fluid property sensor. For example, an external nuclear fluid density sensor may include a gamma ray source and a gamma ray detector, with the source vertically collimated along the axis of the tubing string 18, and with the detector having a coincident axis of collimation, as is used in conventional wireline production logging tools. As another example, an external resistivity sensor may include two toroids (toroidally-shaped magnetic material wound with wire) located in an insulating housing, one toroid being used for excitation, and the other being used for current sensing. In addition, for each of the above sensor types, multiple sensors angularly distributed on the exterior of the tubing string 18 could be utilized.

The sensor 42 is preferably a pressure sensor which, in combination with another pressure sensor 48 in fluid communication with the internal flow passage 40, may be used to determine a pressure differential between the flow passage 40 and the portion of the annulus 22 in which the fluid 38 flows. Alternatively, a single differential pressure sensor (such as the differential pressure sensor 62 shown in FIG. 3) may be used in place of the separate pressure sensors 42, 48.

In addition, internal sensors 50, 52 may be used to sense properties of fluid in the flow passage 40 downstream of the port 32. The sensors 50, 52 may be any of a nuclear fluid density sensor, a nuclear magnetic resonance sensor, an optical attenuation sensor, an optical transmission sensor, an electromagnetic wave sensor or any other type of fluid property sensor.

With external sensors (such as the sensors 42, 44, 46 utilized for sensing properties of the fluid 38) being utilized for fluid flowing from each of the other zones 14, 16, as well as for the zone 12 as shown in FIG. 2, it is possible to individually determine properties of fluid flowing from each of the zones in the method 10. In this manner, informed decisions may be made as to whether to open, close, or to what degree to regulate fluid flow through, each of the flow control devices 26, 28, 30.

Figure 3:
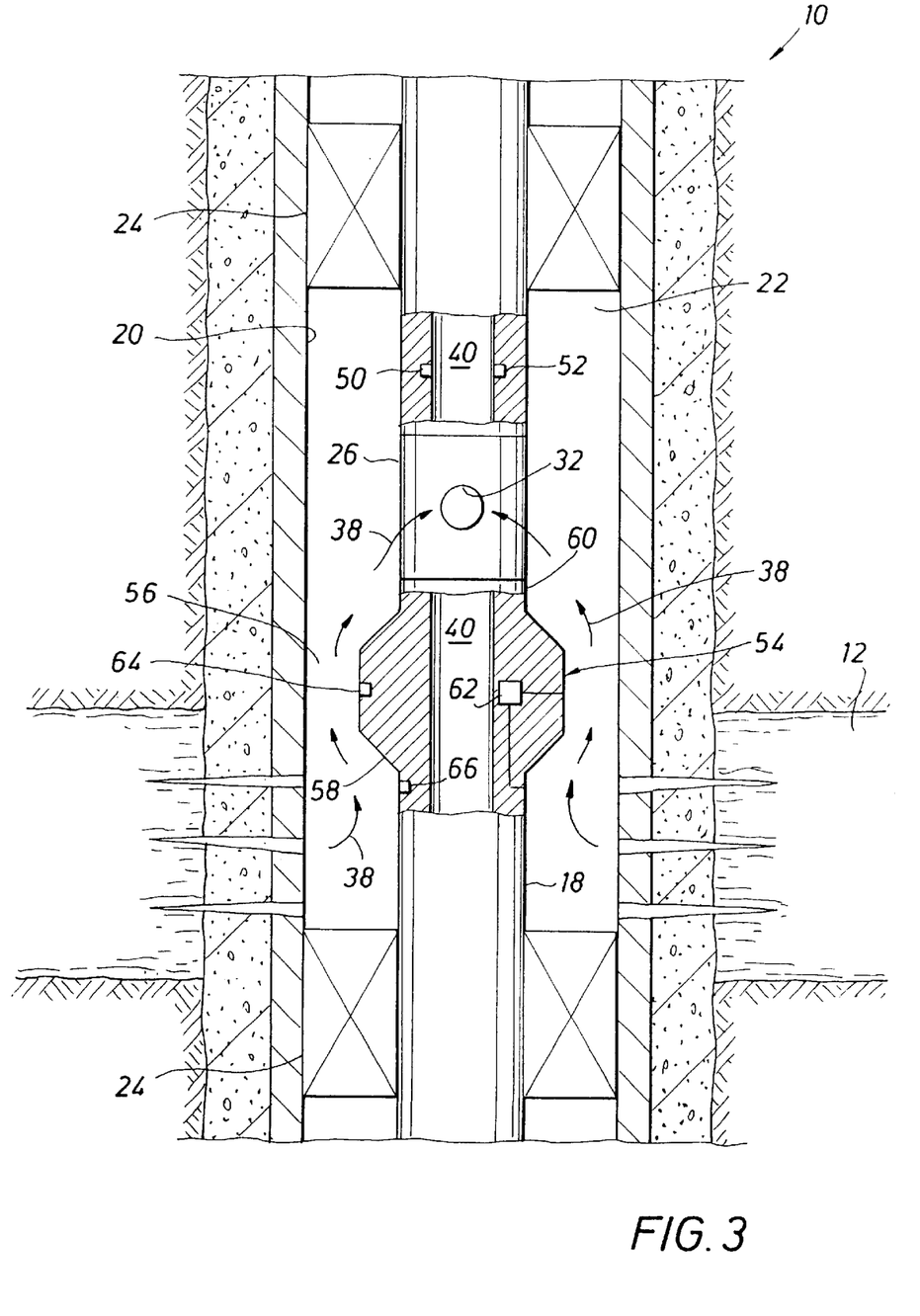
FIG. 3 is an enlarged scale schematic partially cross-sectional view of a second sensor system for an individual zone of a multizone completion, the sensor system being usable in the first method of FIG. 1 and embodying principles of the present invention.

Referring additionally now to FIG. 3, the method 10 is representatively illustrated wherein an external venturi flowmeter 54 is utilized as one of the external sensors for sensing properties of the fluid 38 flowing from the zone 12 into the tubing string 18. Specifically, the flowmeter 54 is used to sense a rate of flow of the fluid 38 through the annulus 22 between the zone 12 and the port 32.

The flowmeter 54 is configured to form a flow restriction 56 in the annulus 22. The flow restriction 56 is defined between the wellbore 20 and a radially outwardly extending projection 58 formed on a housing 60 of the flowmeter 54. It will be readily appreciated by one skilled in the art that a pressure of the fluid 38 decreases as it accelerates to flow through the restriction. The flow restriction 56, therefore, creates a venturi effect external to the tubing string 18.

Preferably, a differential pressure sensor 62 is used to sense a pressure differential between the fluid 38 upstream of the flow restriction 56 and the fluid in the flow restriction. From this information, appropriately calibrated, a flow rate of the fluid 38 may be readily determined. Alternatively, other types of sensors, such as individual pressure and temperature sensors 64, 66, may be used to sense properties of the fluid 38.

Note that the sensors 42, 44, 46, 48, 50, 52 described above in relation to FIG. 2 may also be used in conjunction with the flow meter 54 in the method 10 as depicted in FIG. 3.

Figure 4:
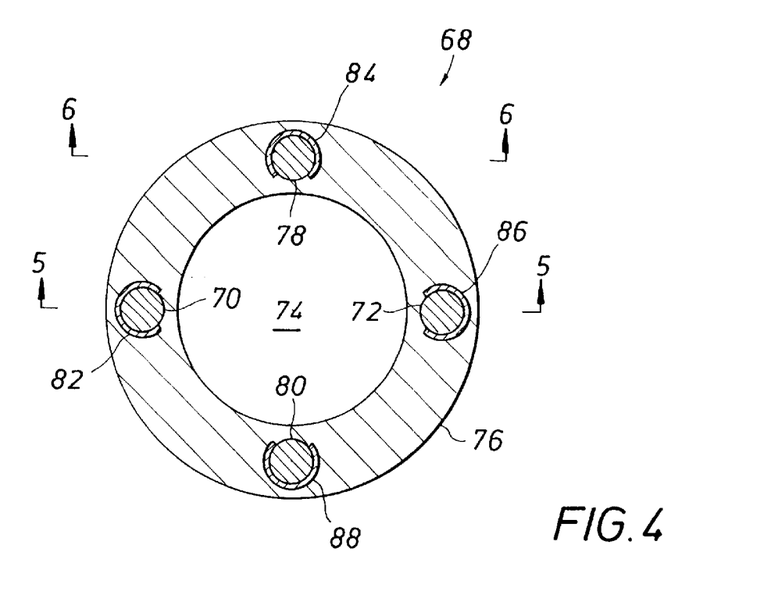
FIG. 4 is a schematic cross-sectional view of a fluid density sensor embodying principles of the present invention.

Referring additionally now to FIG. 4, a fluid density sensor 68 embodying principles of the present invention is representatively illustrated. The sensor 68 may be used in the method 10 described above, in another method described below, or in any other method.

The sensor 68 uniquely utilizes a gamma ray source 70 and a Geiger-Muller gamma ray detector 72 positioned on opposing sides of a flow passage 74 extending longitudinally through a generally tubular housing assembly 76. The source 70 and detector 72 are positioned in a sidewall of the housing 76.

Note that it is not necessary in keeping with the principles of the invention for the sensor 68 to include the Geiger-Muller gamma ray detector 72. For example, scintillation crystals attached to photodiodes, or another type of gamma ray detector, may be utilized in the sensor 68.

Figure 5:
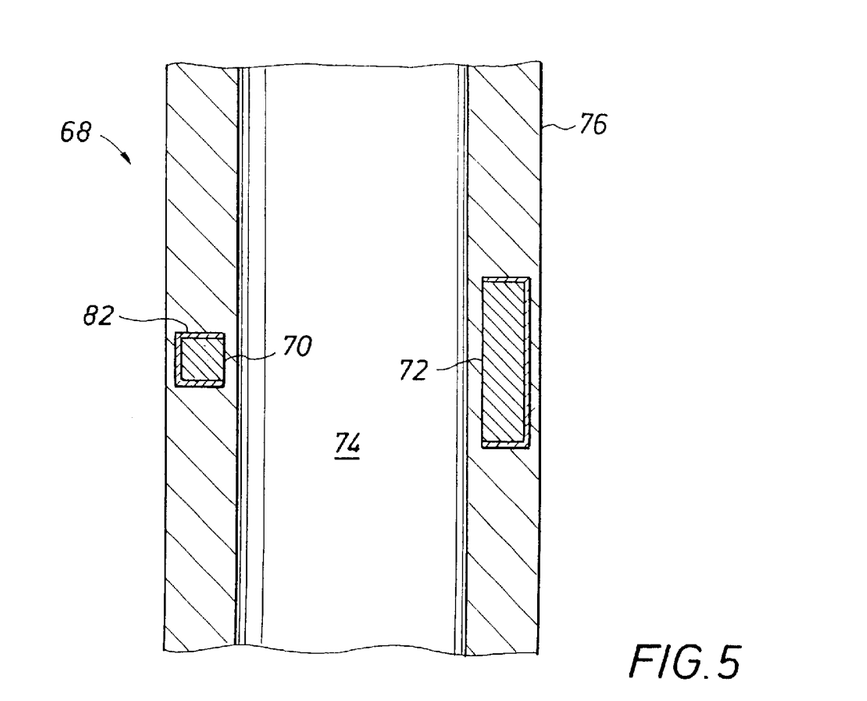
FIG. 5 is a schematic cross-sectional view of the fluid density sensor, taken along line 5—5 of FIG. 4.

The housing 76 is configured for interconnection as a part of a tubular string, such as a production tubing string, in a well. FIG. 5 shows a preferred orientation of the source 70 and detector 72 relative to a longitudinal axis of the flow passage 74.

Preferably, the source 70 is a material having a gamma ray intensity which is exempt from regulations requiring periodic wipe testing thereof. In this manner, the sensor 68 may be included in a tubing string which remains in a well for a substantial length of time, perhaps many years. For example, the source 70 may include one or more individual portions having an intensity of approximately 10 microcuries or less, and may comprise barium 133 or cesium 137 material. Of course, other types of gamma ray sources may be utilized in the sensor 68, without departing from the principles of the present invention.

Fluid flowing through the flow passage 74 will attenuate a rate of gamma rays detected by the detector 72 from the source 70. This attenuation of gamma rays may be related to a density of the fluid flowing through the flow passage 74 upon appropriate calibration of the sensor 68 measurements. If, however, the fluid in the flow passage 74 is nonuniform, such as if the fluid is in multiple phases which have become segregated in the flow passage, the density indicated by the rate of gamma rays detected by the detector 72 from the source 70 may not be truly representative of the overall fluid density.

The inventors have solved the problem of nonuniformity in the fluid flowing through the passage 74 by including a second set of source 78 and detector 80 similar to the source 70 and detector 72 described above. The source 78 is preferably positioned 90 degrees from the source 70 relative to the flow passage, and the detector 80 is preferably positioned 90 degrees from the detector 72 relative to the flow passage. In this manner, the additional source 78 and detector 80 provide a different perspective relative to the flow passage 74 for sensing the fluid density, which aids in resolving any nonuniformity in the fluid. For example, measurements from the detectors 72, 80 may be averaged together. Additionally, the second set of source 78 and detector 80 provide redundancy in the event that one or both of the source 70 and detector 72 should become unusable.

Other quantities of sources and detectors may be used. For example, only the single set of source 70 and detector 72 may be used, three or more sets of sources and detectors may be used, etc.

Each of the sources 70, 78 and each of the detectors 72, 80 is collimated by shielding 82, 84, 86, 88, respectively. The shielding 82 directs gamma rays from the source 70 toward the detector 72, the shielding 84 directs gamma rays from the source 78 toward the detector 80, the shielding 86 permits the detector 72 to receive gamma rays substantially only from a direction of the source 70, and the shielding 88 permits the detector 80 to receive gamma rays substantially only from a direction of the source 78.

The shieldings 82, 84, 86, 88 minimize interference between each set of source and detector. It is, however, recognized that some gamma rays originating from the source 70 may be received by the detector 80 and some gamma rays originating from the source 78 may be received by the detector 72. In addition, some background gamma radiation from background sources, such as earth formations, scale buildup in the flow passage 74, etc., may be received by the detectors 72, 80, even through their shielding 86, 88.

Figure 6:
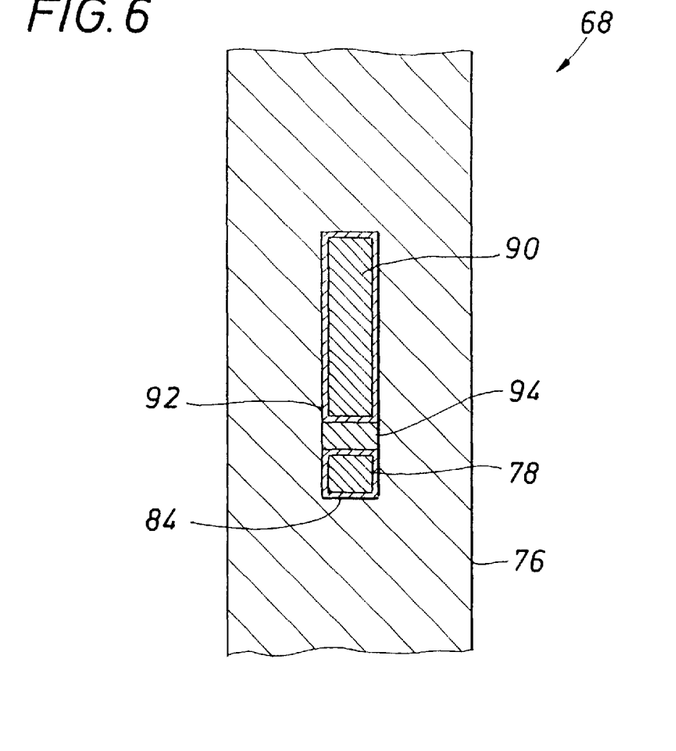
FIG. 6 is a schematic cross-sectional view of the fluid density sensor, taken along line 6—6 of FIG. 4.

Referring additionally now to FIG. 6, a cross-sectional view of the sensor 68 is representatively illustrated, in which it may be seen that another detector 90 is positioned in the housing 76 sidewall above the source 78. The detector 90 is similar to the other detectors 72, 80 described above. The detector 90 is used to compensate for background gamma radiation received by the sensors 72, 80.

The detector 90 has shielding 92 on all sides. The shielding 92 is preferably, but not necessarily, made of the same material as used for the shielding 86, 88. In this manner, the detector 90 should receive approximately the same amount of background radiation through its shielding as received by the detectors 72, 80. However, the detector 90 could receive a different amount of background radiation, or be otherwise shielded, without departing from the principles of the present invention.

In addition, the detector 90 may receive through its shielding 92 some gamma rays originating from the sources 70, 78. Due to the close proximity of the detector 90 to the source 78, a shield 94 may be positioned between the source 78 and the detector 90 to prevent any gamma rays from traveling in a straight line from the source 78 to the detector 90. The shield 94 may be made of tungsten and may be incorporated into either or both of the shieldings 84, 92.

Prior to running the sensor 68 into a well, the rates of gamma rays received by the detector 90 from each of the sources 70, 78 may be conveniently measured by merely assembling the sensor 68 and recording the gamma ray count rate from the detector 90. Then, after the sensor 68 has been interconnected in a tubing string and positioned in a well, this gamma ray count rate due to the sources 70, 78 may be subtracted from the gamma ray count rate from the detector 90 in the well, to obtain a measurement of the background gamma ray count rate. Of course, a more complex mathematical operation than mere subtraction may be used to compensate for the gamma ray count rate due to the sources 70, 78 and obtain a measurement of the background count rate.

The background gamma ray count rate as determined by using the detector 90 may then be subtracted from the gamma ray count rates as measured by each of the detectors 72, 80 to thereby determine more accurately the actual gamma ray count rates received by each of the detectors 72, 80 from the respective one of the sources 70, 78. Again, a more complex mathematical operation than mere subtraction may be used to compensate for the background count rate and obtain the count rates received by the detectors 72, 80 from the respective sources 70, 78.

Figure 7:
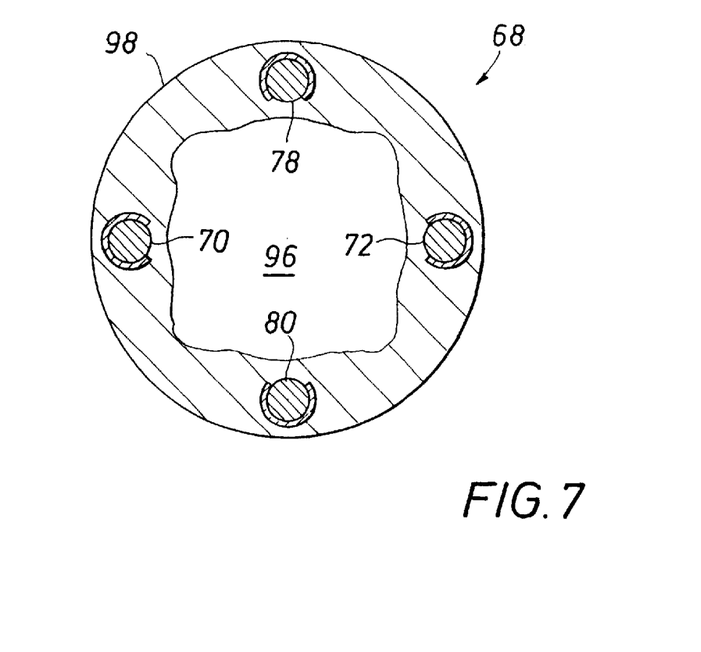
FIG. 7 is a schematic cross-sectional view of the fluid density sensor, showing an alternate configuration thereof.

Referring additionally now to FIG. 7, an alternate configuration of the sensor 68 is representatively illustrated. In this configuration, the sensor 68 includes a differently formed flow passage 96 extending through a housing 98. A cross-section of the flow passage 96 taken perpendicular to its longitudinal axis is noncircular, as depicted in FIG. 7. Specifically, the flow passage 96 perimeter extends radially outward somewhat between adjacent ones of the sources 70, 78 and detectors 72, 80.

The noncircular shape of the flow passage 96 provides more flow area, thereby decreasing a resistance to fluid flow therethrough and decreasing the velocity of the fluid flow. This may reduce the susceptibility of the housing 98 to erosion.

Figure 8:
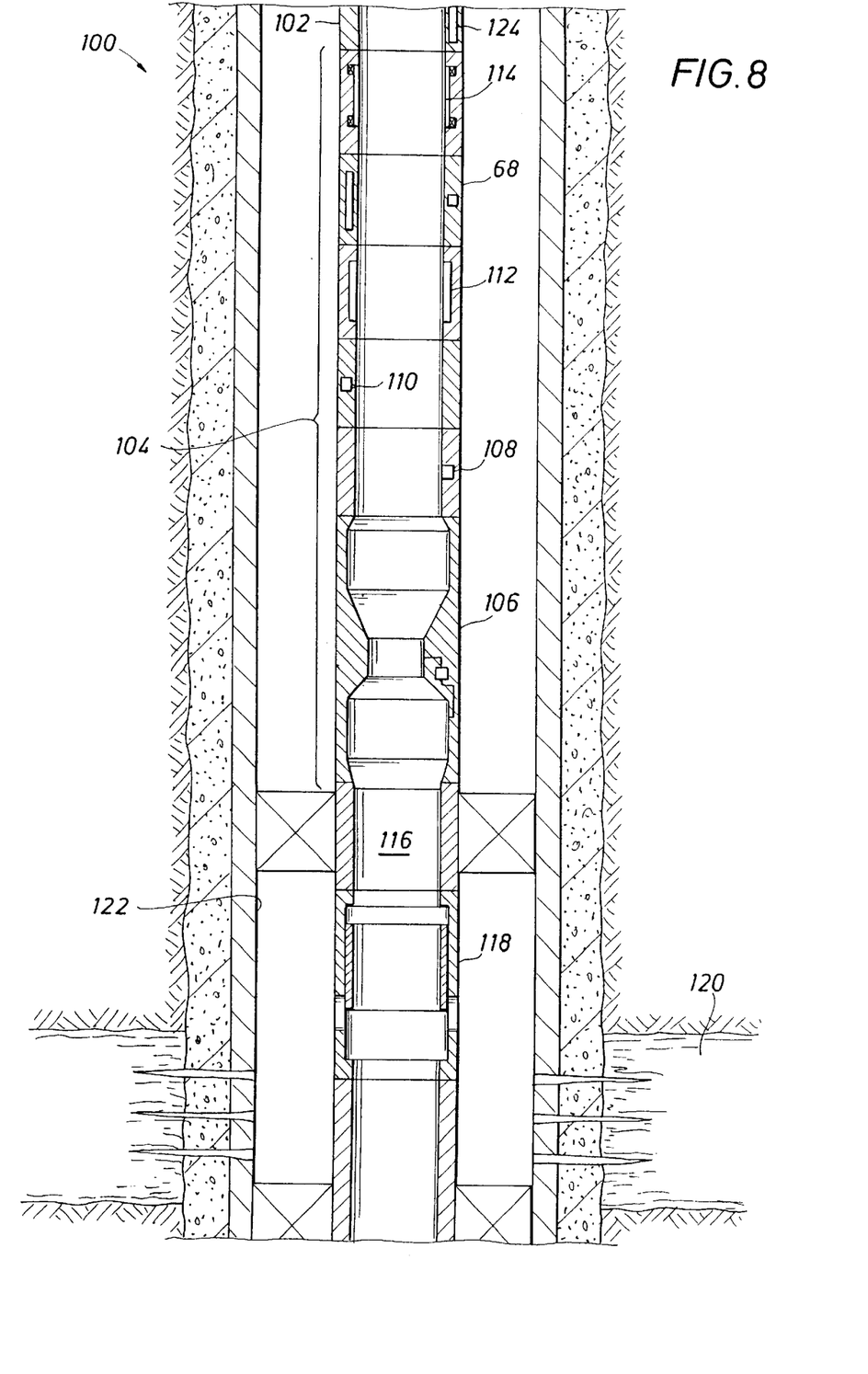
FIG. 8 is a schematic view of a second method of sensing fluid properties in a subterranean well utilizing a second sensor system, the second method and sensor system embodying principles of the present invention.

Referring additionally now to FIG. 8, another method 100 embodying principles of the present invention is representatively illustrated. In the method 100, the fluid density sensor 68 is interconnected in a tubular string 102 as a part of an overall sensor system 104. Of course, another type of fluid density sensor may be used in the sensor system 104, without departing from the principles of the present invention. However, the fluid density sensor 68 is preferred for long term use in the tubular string 102, due to its use of exempt gamma ray sources and durable long-lasting Geiger-Muller detectors.

The sensor system 104 further includes a flowmeter 106, a pressure sensor 108, a temperature sensor 110, and a fluid dielectric sensor 112 and/or a fluid conductivity sensor 114. These sensors 106, 108, 110, 112, 114 may be any of the various corresponding types of sensors well known to those skilled in the art. Of course, other types of sensors may be utilized, without departing from the principles of the present invention.

The inventors have found that, with appropriately calibrated measurements obtained from the combination of sensors 68, 106, 108, 110, 112, 114 illustrated in FIG. 8, a volumetric flow rate of each phase of fluid flowing through an internal flow passage 116 of the tubular string 102 may be obtained.

A flow control device, such as a variable choke 118, interconnected in the tubular string 102 may be used to regulate fluid flow between a zone 120 intersected by a wellbore 122 of the well and the flow passage 116. This regulation of fluid produced from the zone 120 may be performed in response to measurements of fluid properties obtained from the sensor system 104. For example, if the sensor system 104 indicates that water is beginning to be produced from the zone 120, the flow control device 118 may be closed.

Electronic circuitry 124 converts the outputs from the sensors 68, 106, 108, 110, 112, 114 into usable form for transmission to a remote location, such as a computer at the surface. For example, the electronic circuitry 124 may convert the outputs of the detectors 72, 80, 90 into a form indicating the respective gamma ray count rates (gamma ray counts per unit of time) measured by the detectors. Software on the computer at the surface may then convert the count rates into an indicator of fluid density, using known mathematical relationships. The electronic circuitry 124 and the software may be developed using techniques well known to those skilled in the art.

Figure 9:
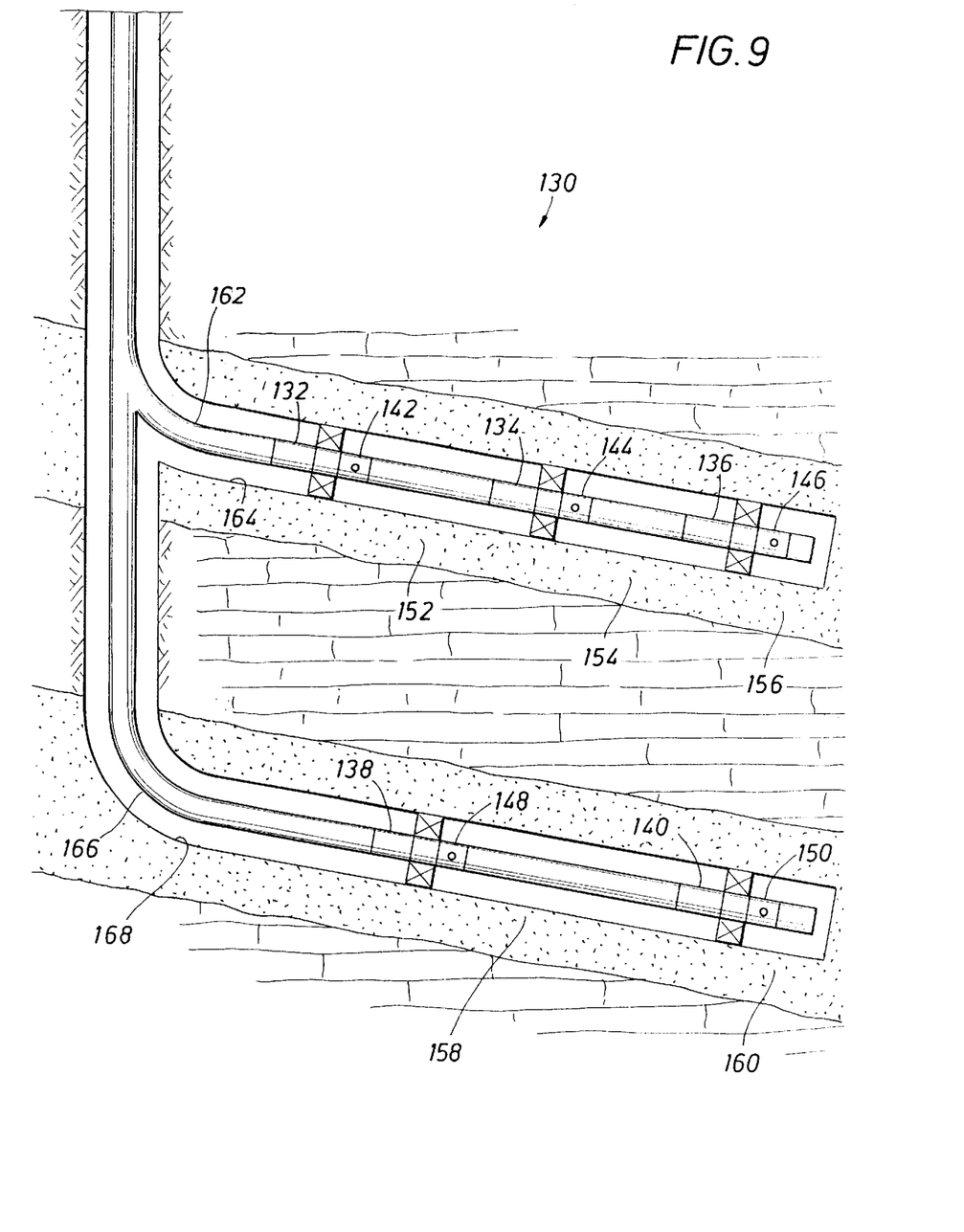
FIG. 9 is a schematic view of a method of calibrating sensor systems in a multilateral well.

Referring additionally now to FIG. 9, another method 130 embodying principles of the present invention is representatively illustrated. The method 130 utilizes multiple sensor systems 132, 134, 136, 138, 140 and multiple flow control devices, such as variable chokes 142, 144, 146, 148, 150, to monitor and control production from corresponding multiple zones 152, 154, 156, 158, 160 of a well.

The sensor systems 132, 134, 136, 138, 140 may be similar to the sensor system 104 described above, and the chokes 142, 144, 146, 148, 150 may be similar to the choke 118 described above. The sensor systems 132, 134, 136 and corresponding respective chokes 142, 144, 146 are interconnected in a tubing string 162 extending into a branch wellbore 164 of the well. The sensor systems 138, 140 and corresponding respective chokes 148, 150 are interconnected in another tubing string 166 extending into a wellbore 168, which may be a branch wellbore or a portion of a main wellbore. It is to be clearly understood, however, that the particular number and arrangement of sensor systems, flow control devices, tubing strings, wellbores, etc. depicted for the method 130 in FIG. 9 are given merely as an example of one embodiment of the invention, and are not to be taken as limiting the principles of the present invention in any way.

In order to be able to determine the volumetric flow rates of each phase of fluid produced from each of the zones 152, 154, 156, 158, 160 using the sensor systems 132, 134, 136, 138, 140, the inventors have found that the measurements obtained from each of the sensor systems should be calibrated while the fluid produced from each of the zones is flowing through the respective sensor systems. Unfortunately, each sensor system will have fluid flowing through it from its corresponding zone as well as from each zone produced upstream therefrom relative to the respective tubing string 162 or 166. For example, the sensor system 132 will have fluid flowing through it from the zones 152, 154, 156 if the chokes 142, 144, 146 are open, making it difficult to calibrate the sensor system for the fluid flowing only from the corresponding zone 152.

The inventors have devised the method 130 for calibrating the sensor systems 132, 134, 136, 138, 140 which resolves these problems. In the method 130, flow is initially permitted through only a lowermost one of the flow control devices in a first one of the tubing strings. As used herein, the term "lowermost" means farthest upstream relative to fluid flow through the corresponding tubing string, or farthest from the surface along the tubing string. The sensor system corresponding to that flow control device is calibrated by measuring properties of the produced fluid at the surface and determining appropriate calibration values for measurements obtained from the corresponding sensor system.

Properties of the produced fluid measured at the surface may include flow rate, oil weight, gas gravity, water density and water salinity. The inventors have found that this combination of measured properties is sufficient to enable calibration of the sensors included in the sensor system 104 described above. Of course, other properties may be measured without departing from the principles of the present invention.

Once the calibration procedure has been performed for the sensor system corresponding to the lowermost flow control device in a tubing string, the next lowermost flow control device is opened. The sensor system corresponding to that next lowermost flow control device is calibrated using the procedure described above, that is, by measuring properties of the produced fluid at the surface and determining appropriate calibration values for measurements obtained from the corresponding sensor system.

The lowermost flow control device is not closed while the next lowermost flow control device is opened, so the fluid properties measured by the sensor system corresponding to the next lowermost flow control device will be indicative of fluid entering the tubing string from both of the two lowermost flow control devices. However, since the fluid properties of the fluid entering the tubing string from the lowermost flow control device have already been determined, appropriate adjustments may be made to the measurements obtained from the sensor system corresponding to the next lowermost flow control device to account for the contribution thereto by the fluid entering the tubing string through the lowermost flow control device.

The above process is repeated, successively opening next lowermost flow control devices in a tubing string and performing the calibration procedure, until all of the flow control devices in a tubing string have been opened and all of the corresponding sensor systems have been calibrated. Then all of the flow control devices in that tubing string are closed and the process is repeated for the next tubing string.

In the method 130, the calibration process would begin by closing all of the chokes 142, 144, 148, 150, except for the lowermost choke 146 in the tubing string 162. Fluid from the zone 156 would be produced into the tubing string 162 and properties of the fluid would be measured at the surface. Appropriate calibration values for the measurements obtained from the sensor system 136 would then be determined.

The next lowermost choke 144 in the tubing string 162 would then be opened and fluid from the zone 154 would be commingled with fluid from the zone 156 in the tubing string. Properties of the fluid produced into the tubing string 162 would be measured at the surface. Appropriate calibration values for the measurements obtained from the sensor system 134 would then be determined, accounting for the contribution to the measured properties of the fluid from the zone 156.

The next lowermost choke 142 in the tubing string 162 would then be opened and fluid from the zone 152 would be commingled with fluid from the zones 154, 156 in the tubing string. Properties of the fluid produced into the tubing string 162 would be measured at the surface. Appropriate calibration values for the measurements obtained from the sensor system 132 would then be determined, accounting for the contribution to the measured properties of the fluid from the zones 154, 156.

All of the chokes 142, 144, 146 in the tubing string 162 would then be closed and the lowermost choke 150 in the tubing string 166 would be opened. Fluid from the zone 160 would be produced into the tubing string 166 and properties of the fluid would be measured at the surface. Appropriate calibration values for the measurements obtained from the sensor system 140 would then be determined.

The next lowermost choke 148 in the tubing string 166 would then be opened and fluid from the zone 158 would be commingled with fluid from the zone 160 in the tubing string. Properties of the fluid produced into the tubing string 166 would be measured at the surface. Appropriate calibration values for the measurements obtained from the sensor system 138 would then be determined, accounting for the contribution to the measured properties of the fluid from the zone 160.

The inventors have found that, using the sensor system 104, and appropriately calibrating the measurements obtained by sensors in the sensor system, the volumetric flow rate of each phase of a multiphase fluid produced through a tubing string may be determined. Using multiple sensor systems and the calibration process as representatively described above for the method 130, the volumetric flow rate of each phase of multiphase fluids from each produced zone of a well may be independently determined. This information enables significantly greater control over well production than has heretofore been possible.

Of course, a person skilled in the art would, upon a careful consideration of the above description of representative embodiments of the invention, readily appreciate that many modifications, additions, substitutions, deletions, and other changes may be made to the specific embodiments, and such changes are contemplated by the principles of the present invention. Accordingly, the foregoing detailed description is to be clearly understood as being given by way of illustration and example only, the spirit and scope of the present invention being limited solely by the appended claims.

What is claimed is:

1. A method of sensing properties of fluid flowing in a subterranean well, the method comprising the steps of:

positioning a tubing string in the well, thereby forming an annulus between the tubing string and a wellbore of the well, the tubing string including multiple ports providing fluid communication between the annulus and an interior flow passage of the tubing string;

isolating portions of the annulus from each other, each annulus portion being in communication with a corresponding one of multiple zones intersected by the well, and each annulus portion being in communication with a corresponding one of the tubing string ports; and sensing at least one property of fluid flowing between each corresponding zone and tubing string port utilizing multiple external sensors, each sensor being in communication with fluid flowing external to the tubing string in a corresponding one of the annulus portions between a corresponding one of the zones and a corresponding one of the tubing string ports.

2. The method according to claim 1, wherein the positioning step further comprises providing the ports formed in flow control devices interconnected in the tubing string.

3. The method according to claim 2, wherein the providing step further comprises providing the flow control devices as chokes configured for regulating a rate of fluid flow through each tubing string port.

4. The method according to claim 1, wherein the external sensors are selected from a group including a fluid capacitance sensor, a fluid dielectric sensor, a fluid conductivity sensor, a nuclear fluid density sensor, an acoustic fluid density sensor, a fluid resistivity sensor, a fluid pressure sensor, a temperature sensor, a fluid compressibility sensor and a fluid pH sensor.

5. The method according to claim 1, wherein the sensing step further comprises sensing at least one property of fluid flowing into each tubing string port utilizing multiple internal sensors, each internal sensor being in communication with fluid flowing from a corresponding one of the tubing string ports into the flow passage.

6. The method according to claim 5, wherein the internal sensors are selected from a group including a nuclear fluid density sensor, a nuclear magnetic resonance sensor, an optical attenuation sensor, an optical transmission sensor and an electromagnetic wave sensor.

7. The method according to claim 1, wherein in the sensing step, each of the external sensors comprises an external venturi flowmeter, each of the flowmeters including a flow restriction in the corresponding one of the annulus portions external to the tubing string.

8. The method according to claim 7, wherein each of the external venturi flowmeters includes a differential pressure sensor sensing at least fluid pressure in a corresponding one of the flow restrictions.

9. The method according to claim 7, wherein the flow restrictions are positioned in multiple flowpaths, each of the flowpaths extending between a corresponding one of the zones and a corresponding one of the tubing string ports.

10. The method according to claim 7, wherein each of the flow restrictions is defined by an external projection formed on a housing of the corresponding one of the flowmeters, each of the housings being interconnected in the tubing string.

11. A method of sensing properties of fluid flowing in a subterranean well, the method comprising the steps of:

positioning a tubing string in the well, thereby forming an annulus between the tubing string and a wellbore of the well, the tubing string including multiple ports providing fluid communication between the annulus and an interior flow passage of the tubing string;

isolating portions of the annulus from each other, each annulus portion being in communication with a corresponding one of multiple zones intersected by the well, and each annulus portion being in communication with a corresponding one of the tubing string ports; and sensing multiple properties of fluid flowing into each of the ports utilizing multiple sensor systems interconnected in the tubing string, each sensor system being interconnected in the tubing string downstream of a corresponding one of the ports, and each sensor system including a fluid density sensor, a flowmeter, a temperature sensor, a pressure sensor and a selected one of a fluid dielectric sensor and a fluid conductivity sensor.

12. The method according to claim 11, wherein each of the fluid density sensors includes a gamma ray source and a Geiger-Muller gamma ray detector.

13. The method according to claim 11, wherein in the tubing string positioning step, each of the ports is formed in one of multiple flow control devices, each of the flow control devices being operative to regulate a rate of fluid flow through the corresponding port.

14. A method of calibrating multiple sensor systems interconnected in multiple branch tubing strings, each of the tubing strings including multiple flow control devices, each flow control device regulating fluid flow into one of the tubing strings and being positioned upstream of a corresponding one of the sensor systems relative to fluid flow in the corresponding one of the tubing strings, the method comprising the steps of:

closing all flow control devices in all tubing strings other than a first one of the tubing strings; and with only a lowermost one of the flow control devices in the first tubing string being open, and then with successively next lowermost ones of the flow control devices in the first tubing string being opened, performing the following procedure for the open lowermost flow control device, and again performing the procedure after each successively next lowermost flow control device is opened:

a) flowing fluid through the open one or more flow control devices into the first tubing string;
b) measuring at the earth's surface at least one property of fluid flowing from the first tubing string;
c) recording measurements received from sensors of the one or more sensor systems corresponding to the one or more open flow control devices; and
d) determining calibration values for the measurements received from the sensors of the one or more sensor systems corresponding to the one or more open flow control devices.

15. The method according to claim 14, wherein the measuring step further comprises measuring at the earth's surface a flow rate of each phase of the fluid flowing from the first tubing string, a weight of oil produced, a gravity of gas produced, a density of water produced and a salinity of water produced.

16. The method according to claim 14, further comprising the steps of:

closing all flow control devices in all tubing strings other than a second one of the tubing strings; and with only a lowermost one of the flow control devices in the second tubing string being open, and then with successively next lowermost ones of the flow control devices in the second tubing string being opened, performing the following procedure for the open lowermost flow control device in the second tubing string, and again performing the procedure after each successively next lowermost flow control device in the second tubing string is opened:

a) flowing fluid through the open one or more flow control devices into the second tubing string;
b) measuring at the earth's surface at least one property of fluid flowing from the second tubing string;
c) recording measurements received from sensors of the one or more sensor systems corresponding to the one or more open flow control devices in the second tubing string; and
d) determining calibration values for the measurements received from the sensors of the one or more sensor systems corresponding to the one or more open flow control devices in the second tubing string.

17. The method according to claim 16, wherein the step of measuring at the earth's surface at least one property of fluid flowing from the second tubing string further comprises measuring at the earth's surface for the fluid flowing from the second tubing string a flow rate of each phase of the fluid, a weight of oil produced, a gravity of gas produced, a density of water produced and a salinity of water produced.

18. A method of measuring fluid properties of fluid flowing in a subterranean well, the method comprising the steps of:

positioning a tubing string in the well, thereby forming an annulus between the tubing string and a wellbore of the well, the tubing string including multiple ports providing fluid communication between the annulus and an interior flow passage of the tubing string;

isolating portions of the annulus from each other, each annulus portion being in communication with a corresponding one of multiple zones intersected by the well, and each annulus portion being in communication with a corresponding one of the tubing string ports;

sensing at least one property of fluid flowing between each corresponding zone and tubing string port; and calibrating the sensors by measuring properties of the fluid produced at the surface with at least one of the ports closed.

* * * * *